US012125569B2

(12) United States Patent
Narayanswamy et al.

(10) Patent No.: US 12,125,569 B2
(45) Date of Patent: Oct. 22, 2024

(54) BIOMETRICALLY-LINKED ELECTRONIC PROOF OF HEALTH STATUS OF INDIVIDUAL

(71) Applicant: MASTERCARD INTERNATIONAL INCORPORATED, Purchase, NY (US)

(72) Inventors: Raman Narayanswamy, Nashua, NH (US); Przemek Praszczalek, Irvington, NY (US); Antonia Stroeh, New York, NY (US); Paul Michael Musser, Grass Valley, CA (US); Shashi Raghunandan, Old Greenwich, CT (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 575 days.

(21) Appl. No.: 17/226,816

(22) Filed: Apr. 9, 2021

(65) Prior Publication Data

US 2021/0327551 A1 Oct. 21, 2021

Related U.S. Application Data

(60) Provisional application No. 63/008,221, filed on Apr. 10, 2020.

(51) Int. Cl.
*G16H 10/65* (2018.01)
*A61B 5/00* (2006.01)
(Continued)

(52) U.S. Cl.
CPC .......... *G16H 10/65* (2018.01); *A61B 5/0022* (2013.01); *G06F 16/27* (2019.01);
(Continued)

(58) Field of Classification Search
CPC ........ G16H 10/65; G16H 10/40; G16H 40/67; A61B 5/0022; G06F 16/27; G06F 21/32; G06K 19/06037; G06K 19/06112
See application file for complete search history.

(56) References Cited

U.S. PATENT DOCUMENTS 9,928,379 B1 3/2018 Hoffer
10,885,170 B1 * 1/2021 Maliani ................. H04L 9/0643
(Continued)

FOREIGN PATENT DOCUMENTS

CN 104991056 A 10/2015

OTHER PUBLICATIONS

Dheerendra Mishra et al., Security Enhancement of a Biometric based Authentication Scheme for Telecare Medicine Information Systems with Nonce, 38(41) J Med Syst 1-11 (Year: 2014).*

(Continued)

*Primary Examiner* — Jordan L Jackson
(74) *Attorney, Agent, or Firm* — Michael Best & Friedrich LLP (57) ABSTRACT

Biometrically-linked electronic proof of health status of an individual. In one embodiment, an electronic device including a biometric capture circuitry, a memory, and an electronic processor. The biometric capture circuitry configured to capture one or more biometrics of the individual. The electronic processor is configured to receive the one or more biometrics of the individual that are captured by the biometric capture circuitry, generate a biometric token of the individual based on the one or more biometrics, receive information indicative of a health status of the individual, link the information indicative of the health status of the individual to the biometric token, and control the memory to (Continued)

store the biometric token and the information indicative of the health status of the individual that is linked to the biometric token.

17 Claims, 5 Drawing Sheets

(51) Int. Cl.
    *G06F 16/27*     (2019.01)
    *G06F 21/32*     (2013.01)
    *G06K 19/06*     (2006.01)
    *G16H 10/40*     (2018.01)
    *G16H 40/67*     (2018.01)

(52) U.S. Cl.
    CPC .. *G06K 19/06037* (2013.01); *G06K 19/06112* (2013.01); *G16H 10/40* (2018.01); *G16H 40/67* (2018.01); *G06F 21/32* (2013.01)

(56) References Cited

U.S. PATENT DOCUMENTS

| | | |
|---|---|---|
| 2007/0194884 A1 | 8/2007 | Didier et al. |
| 2009/0183008 A1* | 7/2009 | Jobmann ................ G06F 21/34 |
| | | 235/382 |
| 2017/0068785 A1* | 3/2017 | Experton .............. H04W 12/02 |
| 2017/0177797 A1* | 6/2017 | Kurniawan ......... H04L 63/0861 |
| 2017/0264608 A1 | 9/2017 | Moore et al. |
| 2019/0287663 A1* | 9/2019 | Raduchel ............ H04W 12/069 |

OTHER PUBLICATIONS

International Search Report and Written Opinion for Application No. PCT/US2021/026162 dated Jul. 8, 2021 (8 pages).

\* cited by examiner

BIOMETRICALLY-LINKED ELECTRONIC PROOF OF HEALTH STATUS OF INDIVIDUAL

CROSS-REFERENCE TO RELATED APPLICATION

This application claims the benefit of U.S. Provisional Application No. 63/008,221, filed on Apr. 10, 2020, the entire content of which is hereby incorporated by reference.

FIELD OF THE INVENTION

The present disclosure relates generally to proof of a health status of an individual. More specifically, the present disclosure relates to biometrically-linked electronic proof of a health status of an individual.

BACKGROUND

In response to the COVID-19 pandemic, several governments have announced plans to widely conduct serological antibody testing for COVID-19 and to issue immunization certificates to persons testing positive for COVID-19 antibodies. These governments may then identify people resistant to the disease and unable to act as a carrier to infect others based on the immunization certificates issued to individuals testing positive for the COVID-19 antibodies.

With the immunization certificates, individuals may exit isolation, return to work, travel with fewer restrictions, and care for vulnerable populations. Later, as vaccines are made available, recipients of the vaccine would presumably receive the same proof of immunity with the immunization certificate or an existing immunization certificate may be updated to indicate receipt of the vaccine.

The COVID-19 pandemic has necessitated the physical isolation of entire countries, which in turn has taken an unprecedented toll on the global economy. A proof of immunity (which, conventionally, has been difficult to prove) has real and substantial economic value because individuals that have proof of immunity will be able to work and individuals that do not have proof of immunity may be excluded from the economy. With a real and substantial economic value, the proof of immunity is then susceptible to fraud and tampering because individuals have an incentive to forge documents or bribe a test administrator in order to prevent any exclusion from the economy. In addition, the process of proving immunity may also have the undesired effect of exposing sensitive patient-linked personally identifiable information (referred to herein as "sensitive PII").

SUMMARY

By combining the science of immunity with privacy-respecting proof of immunity, the present disclosure provides for biometrically-linked electronic proof of a health status of an individual that is not indicative of any of an individual's sensitive PII. The biometrically-linked electronic proof discussed in the present disclosure will significantly speed up both local economic and social re-integration and lessen the need for invasive quarantine monitoring.

In one embodiment, the present disclosure includes an electronic device. The electronic device includes a biometric capture circuitry, a memory, and an electronic processor communicatively connected to the memory and the biometric capture circuitry. The biometric capture circuitry configured to capture one or more biometrics of an individual. The memory storing an inclusive identity application. The electronic processor, when executing the inclusive identity application, is configured to receive the one or more biometrics of the individual that are captured by the biometric capture circuitry, generate a biometric token of the individual based on the one or more biometrics, receive information indicative of a health status of the individual, link the information indicative of the health status of the individual to the biometric token, and control the memory to store the biometric token and the information indicative of the health status of the individual that is linked to the biometric token. The information indicative of the health status of the individual that is linked to the biometric token is biometrically-linked electronic proof of the health status of the individual.

In another embodiment, the present disclosure includes a non-transitory computer-readable medium storing instructions that, when executed by an electronic processor, cause the electronic processor to perform a set of operations. The set of operations includes receiving one or more biometrics of an individual that are captured by a biometric capture circuitry. The set of operations includes generating a biometric token of the individual based on the one or more biometrics. The set of operations includes receiving information indicative of a health status of the individual. The set of operations includes linking the information indicative of the health status of the individual to the biometric token. The set of operations also includes controlling a memory to store the biometric token and the information indicative of the health status of the individual that is linked to the biometric token. The information indicative of the health status of the individual that is linked to the biometric token is biometrically-linked electronic proof of the health status of the individual.

In yet another embodiment, the present disclosure includes a system including a network, a server, and a first electronic device. The server including a first communication interface configured to communicate with the network, a first electronic processor, and a first memory including an immunization collection and issuance program and a global ledger. The first electronic device communicatively connected to the network. The first electronic processor, when executing the immunization collection and issuance program, is configured to receive a biometric token of an individual from the first electronic device via the first communication interface and the network, receive information indicative of a health status of the individual via the first communication interface and the network, determine whether the information indicative of the health status of the individual is linked to the biometric token, and responsive to determining that the information indicative of the health status is linked to the biometric token, control the first memory to store the biometric token and the information indicative of the health status of the individual in the global ledger. The information indicative of the health status of the individual that is linked to the biometric token is biometrically-linked electronic proof of the health status of the individual.

DETAILED DESCRIPTION

Before any embodiments of the present disclosure are explained in detail, it is to be understood that the present disclosure is not limited in its application to the details of construction and the arrangement of components set forth in the following description or illustrated in the following drawings. The present disclosure is capable of other embodiments and of being practiced or of being carried out in various ways.

Figure 1:
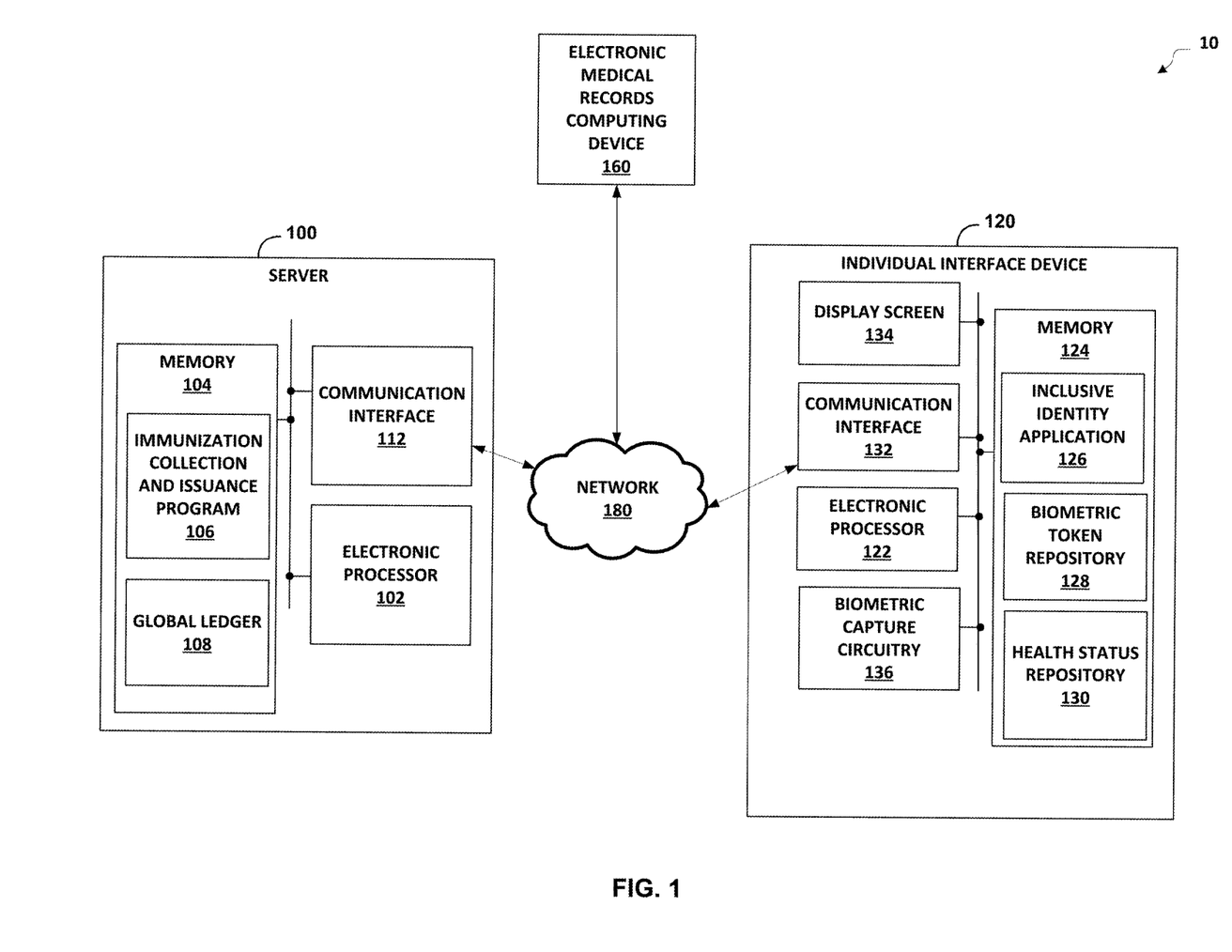
FIG. 1 is a block diagram illustrating a system that provides biometrically-linked electronic proof of a health status of an individual, in accordance with various aspects of the present disclosure.

FIG. 1 is a block diagram illustrating a system 10 that provides biometrically-linked electronic proof of a health status of an individual. It should be understood that, in some embodiments, there are different configurations from the configuration illustrated in FIG. 1. The functionality described herein may be extended to any number of servers providing distributed processing.

In the example of FIG. 1, the system 10 includes a server 100, an individual interface device 120, an electronic medical records computing device 160, and a network 180. The server 100 includes an electronic processor 102 (for example, a microprocessor or another suitable processing device), a memory 104 (for example, a non-transitory computer-readable medium or a non-transitory computer-readable storage medium), and a communication interface 112. It should be understood that, in some embodiments, the server 100 may include fewer or additional components in configurations different from that illustrated in FIG. 1. Also the server 100 may perform additional functionality than the functionality described herein. In addition, the functionality of the server 100 may be incorporated into other servers (for example, the functionality of the server 100 may be incorporated into the electronic medical records computing device 160). As illustrated in FIG. 1, the electronic processor 102, the memory 104, and the communication interface 112 are electrically coupled by one or more control or data buses enabling communication between the components.

The electronic processor 102 executes machine-readable instructions stored in the memory 104. For example, the electronic processor 102 may execute instructions stored in the memory 104 to perform the functionality described herein.

The memory 104 may include a program storage area (for example, read only memory (ROM)) and a data storage area (for example, random access memory (RAM), and other non-transitory, machine-readable medium). In some examples, the program storage area may store machine-executable instructions regarding an available resources and options collection program 106 (hereinafter "immunization collection and issuance program 106"). In some examples, the data storage area may store data regarding a global ledger 108.

The immunization collection and issuance program 106 causes the electronic processor 102 to collect and update the health status of an individual, the health status of the individual being stored in the global ledger 108. In some examples, the immunization collection and issuance program 106 causes the electronic processor 102 to collect and update the health status (e.g., positive test results of a serological test or proof of vaccination) of the individual based on inputs received from an external device. For example, the electronic processor 102 may receive the aforementioned inputs from a verified medical professional to update the global ledger 108 via the electronic medical records computing device 160 and the network 180. Alternatively, the electronic processor 102 may receive the aforementioned inputs from an individual to update the global ledger 108 via the individual interface device 120 and the network 180.

In some examples, the global ledger 108 is a central repository of health statuses (e.g., immunization records, results of serological testing, or other suitable health statuses) regarding a plurality of individuals. Each of the health statuses is associated with a biometric token of a specific individual (also referred to herein as "linked"). The health statuses may be updated periodically with the immunization collection and issuance program 106 as described above.

The biometric token of the specific individual is also not reflective of any sensitive PII. Sensitive PII is any information that may be used to identify an individual without additional information (e.g., an individual's social security number, an individual's name and date-of-birth, an individual's address, an individual's driver license number, an individual's passport number, an individual's different biometrics, or other suitable sensitive PII). The biometric token of the specific individual may instead be indicative of non-sensitive personally identifiable information that requires additional information (e.g., a unique hashing algorithm applied to an individual's different biometrics). In some examples, the biometric token is a biometric hash generated by the unique hashing algorithm.

The communication interface 112 receives data from and provides data to devices external to the server 100, such as the individual interface device 120 and the electronic medical records computing device 160 via the network 180. For example, the communication interface 112 may include a port or connection for receiving a wired connection (for example, an Ethernet cable, fiber optic cable, a telephone cable, or the like), a wireless transceiver, or a combination thereof. In some examples, the communication interface includes an radio frequency identifier (RFID) reader. In some examples, the network 180 is the Internet.

In the example of FIG. 1, the individual interface device 120 (also referred to herein as "an electronic device" or "a display device") includes an electronic processor 122 (for example, a microprocessor or another suitable processing device), a memory 124 (for example, a non-transitory computer-readable storage medium), a communication interface 132, a display screen 134, and a biometric capture circuitry 136. It should be understood that, in some embodiments, the individual interface device 120 may include fewer or additional components in configurations different from that illustrated in FIG. 1. Also the individual interface device 120 may perform additional functionality than the functionality described herein. In addition, some of the functionality of the individual interface device 120 may be incorporated into other servers (e.g., incorporated into the server 100). As illustrated in FIG. 1, the electronic processor 122, the memory 124, the communication interface 132, the display screen 134, and the biometric capture circuitry 136 are electrically coupled by one or more control or data buses enabling communication between the components.

The electronic processor 122 executes machine-readable instructions stored in the memory 124. For example, the electronic processor 122 may execute instructions stored in the memory 124 to perform the functionality described herein.

The memory 124 may include a program storage area (for example, read only memory (ROM)) and a data storage area (for example, random access memory (RAM), and other non-transitory, machine-readable medium). The program storage area includes an inclusive identity application 126. In some examples, the inclusive identity application 126 may be a standalone application. In other examples, the inclusive identity application 126 is a feature that is part of a separate application (e.g., the inclusive identity application 126 may be included as part of a camera application, a banking application, or other suitable application). The data storage area includes an biometric token repository 128 and a health status repository 130.

The inclusive identity application 126 causes the electronic processor 122 to generate a biometric token from the biometric information captured by the biometric capture circuitry 136. For example, when the biometric capture circuitry 136 is a camera, the inclusive identity application 126 causes the electronic processor 122 to generate a biometric token from an individual's facial image captured by the camera. The biometric token may be a biometric hash and generated by a unique biometric hashing algorithm, e.g., a biometric hashing algorithm developed by TrustStamp®.

In some examples, the inclusive identity application 126 causes the electronic processor 122 to control the biometric token repository 128 to temporarily store the biometric token. In other examples, the inclusive identity application 126 causes the electronic processor 122 to control the biometric token repository 128 to permanently store the biometric token.

The inclusive identity application 126 also causes the electronic processor 122 to store any input indicative of the health status of the individual in the health status repository 130. For example, any input indicative of an immunization or positive results of serological testing of the individual may be stored in the health status repository 130.

The inclusive identity application 126 also causes the electronic processor 122 to link any input indicative of the health status of the individual to the biometric token that is generated and stored in the biometric token repository 128. For example, any input indicative of an immunization or positive results of serological testing of the individual is linked to the biometric token of the individual. Responsive to linking any input indicative of the health status of the individual to the biometric token that is generated and stored in the biometric token repository 128, the inclusive identity application 126 causes the electronic processor 122 to output the biometric token and the linked health status to the server 100.

The inclusive identity application 126 causes the electronic processor 122 to generate one or more graphical user interfaces. The inclusive identity application 126 also causes the electronic processor 122 to control the display screen 134 to display the one or more graphical user interfaces. In some examples, the individual interface device 120 is a smartphone and the display screen 134 is a presence-sensitive display screen.

In some examples, the individual interface device 120 includes one or more user interfaces (not shown). The one or more user interfaces include one or more input mechanisms (for example, a touch screen, a keypad, a button, a knob, and the like), one or more output mechanisms (for example, a display, a speaker, and the like), or a combination thereof. The one or more optional user interfaces receive input from a user (e.g., a verified medical professional or an individual), provide output to a user, or a combination thereof. In some examples, as an alternative to or in addition to managing inputs and outputs through the one or more optional user interfaces, the individual interface device 120 may receive user input, provide user output, or both by communicating with an external device (e.g., the server 100) over a wired or wireless connection.

The communication interface 132 receives data from and provides data to devices external to the individual interface device 120, i.e., the server 100 and the electronic medical records computing device 160. For example, the communication interface 132 may include a port or connection for receiving a wired connection (for example, an Ethernet cable, fiber optic cable, a telephone cable, or the like), a wireless transceiver, or a combination thereof. In some examples, the communication interface 132 may be communicatively connected to the communication interface 112 via a backhaul (not shown).

The display screen 134 is an array of pixels that generates and outputs images including information regarding the biometric token to a user. In some examples, the display screen 134 is one of a liquid crystal display (LCD) screen, a light-emitting diode (LED) and liquid crystal display (LCD) screen, a quantum dot light-emitting diode (QLED) display screen, an interferometric modulator display (IMOD) screen, a micro light-emitting diode display screen (mLED), a virtual retinal display screen, or other suitable display screen.

The biometric capture circuitry 136 is any electronic circuitry that is configured to capture one or more biometric characteristics of an individual. For example, the biometric capture circuitry 136 may be a camera with an image sensor that generates and outputs image data of the individual. In some examples, the image sensor may be a semiconductor charge-coupled device (CCD) image sensor, a complementary metal-oxide-semiconductor (CMOS) image sensor, or other suitable image sensor. The electronic processor 122 receives the biometric data of the subject that is output by the biometric capture circuitry 136.

The system 10 is self-sovereign because the individual has ownership over their proof credentials stored in the server 100, and there is no storage of sensitive PII data. The server 100 mitigates the risk of discrimination against non-immune populations and puts the individual in control of sharing their health status. In some examples, the health status may be a digital International Certificate of Vaccination (ICV) that is electronically stored by the server 100, but without any PII information. The individual may choose to produce the evidence of at any entity to provide their vaccination credentials. However, the individual may also choose not to share their health status as well.

The system 10 relies on a zero-knowledge proof because attestation of immunity does not require the individual to share other irrelevant information like demographics or medical records. The paper-based ICV does contain a name, date of birth, and a trail of clinicians and dates on which various vaccines or immunity attestation were granted. However, the paper-based ICV does not contain relevant health data or even citizenship.

The system 10 is interoperable because any accredited clinic or lab around the world may provide the biometrically-linked electronic proof of an individual's health status to the server 100. Additionally, any entity (e.g., any government or employer) may access the biometrically-linked electronic proof of an individual's health status by querying the server 100.

The system 10 also provides secure authentication because the biometrically-linked electronic proof stored on the server 100 cannot easily be tampered with or forged. Additionally, the biometrically-linked electronic proof stored on the server 100 is easily verifiable because a government or an employer is able to audit the authenticity of the biometrically-linked electronic proof.

The system 10 is also cost effective because the biometrically-linked electronic proof may be issued and authenticated in "resource constrained" environments. For example, the biometrically-linked electronic proof may be issued and authenticated in low-income countries with little digital infrastructure, poor connectivity, and low digital literacy among healthcare workers and employers.

Figure 2:
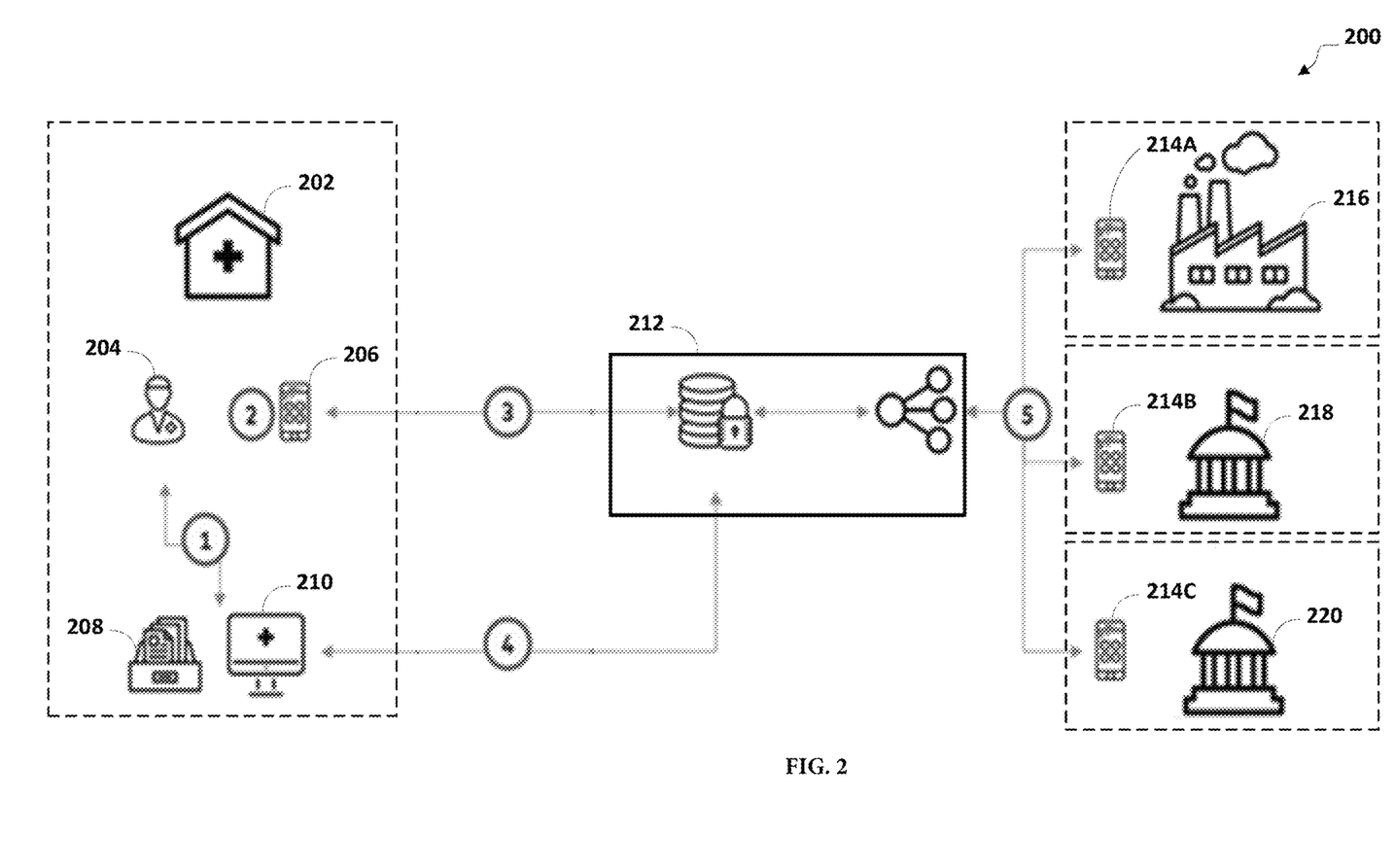
FIG. 2 is a diagram illustrating a system that provides biometrically-linked electronic proof of a health status of an individual, in accordance with various aspects of the present disclosure.

FIG. 2 is a diagram illustrating a system 200 that provides biometrically-linked electronic proof of a health status of an individual. In the example of FIG. 2, the system 200 includes a diagnostic lab 202, a lab technician 204, an individual interface device 206, a paper file 208, an electronic medical record computing device 210, a central server 212, a plurality of individual interface devices 214A-214C, a prospective employer 216, a first foreign customs 218, and a second foreign customs 220.

The individual interface device 206 and the plurality of individual interface devices 214A-214C may be similar to or the same as the individual interface device 120 as described above in FIG. 1. In some examples, the individual interface device 206 and the plurality of individual interface devices 214A-214C are the same electronic device. In other examples, the individual interface device 206 and the plurality of individual interface devices 214A-214C are different electronic devices. In yet other examples, two of the individual interface device 206 and the plurality of individual interface devices 214A-214C may be the same electronic device.

The electronic medical record computing device 210 may be similar to or the same as the electronic medical records computing device 160 as described above in FIG. 1. The central server 212 may be similar to or the same as the server 100 as described above in FIG. 1.

In the example of FIG. 2, and in a developed market, an individual downloads the inclusive identity application 126 onto the individual interface device 206 and self-registers with the inclusive identity application 126 by capturing one or more of the individual's biometrics. For example, the inclusive identity application 126 may cause an electronic processor of the individual interface device 206 to capture one or more of the individual's biometrics with biometric capture circuitry. The inclusive identity application 126 generates a QR code as part of the registration process. In some examples, the QR code is indicia that represents the individual's biometric token generated by the inclusive identity application 126 and based on the captured biometrics.

The lab technician 204 scans the QR code (e.g., displayed on the display screen of the individual interface device 206) and enters the remaining personal information of the individual into the local computing device available at the diagnostic lab 202 (e.g., the electronic medical records computing device 160). If a serological test of the individual is positive or if the individual receives a vaccine (meaning the individual is immune to a specific disease), the lab technician 204 updates the record against the individual and based on the QR code (e.g., updates the paper file 208 or an electronic record stored in the electronic medical record computing device 210). All other personally identifiable information of the individual will continue to be stored at the diagnostic lab 202 per normal procedures, i.e., stored in the paper file 208 or the electronic medical record computing device 210, and according to local laws and regulations.

In some examples, when the individual receives the results of the serological test, the individual may scan the test results generated by the diagnostic lab 202 with the biometric capture circuitry and the inclusive identity application 126 causes the electronic processor to control a memory to store the results. For example, the inclusive identity application 126 may cause the electronic processor of the individual interface device 206 to transmit the test results to the central server 112 for storage in a central database. Additionally or alternatively, the inclusive identity application 126 may cause the electronic processor of the individual interface device 206 to control an internal memory to store the test results (e.g., the health status repository 130).

In other examples, when the individual interface device 206 receives the results of the serological test in an electronic format, the inclusive identity application 126 causes the electronic processor of the individual interface device 206 to control a memory to store the results. For example, the inclusive identity application 126 may cause the electronic processor of the individual interface device 206 to automatically transmit the test results to the central server 112 for storage in a central database. Additionally or alternatively, the inclusive identity application 126 may cause the electronic processor of the individual interface device 206 to control an internal memory to store the test results (e.g., store the test results in the health status repository 130).

There are multiple types of entities that might want or need access to the individual's biometrically-linked electronic proof of immunization. For example, domestic and foreign government officials, employers, healthcare and at-risk care facilities, schools, or other suitable entities may request the individual's biometrically-linked electronic proof of immunization. As illustrated in FIG. 2, these entities include a prospective employer 216, a first foreign customs entity 218, and a second foreign customs entity 220 and are referred to as "a prospective checker."

A prospective checker that needs to authenticate the immunity of an individual would also have access to the inclusive identity application 126 via one of the plurality of individual interface devices 214A-214C. At the point of validation request, the checker uses one of the plurality of individual interface devices 214A-214C to scan the QR code of the individual. For example, the one of the plurality of individual interface devices 214A-214C may include a camera that scans the QR code. Alternatively, the one of the plurality of individual interface devices 214A-214C may be electrically or communicatively connected to a QR code scanner that scans the individual's QR code. The one of the plurality of individual interface devices 214A-214C may use the scan of the QR code to retrieve the relevant status of the test results from the central server 212. Further, in a case where additional verification is required, the scan of the QR code may be matched against the biometrics of the individual by using the inclusive identify application 126 to generate a comparison QR code with the same biometric used to register for the inclusive identity application 126.

In the example of FIG. 2, and in a developing market, the lab technician 204 may use the inclusive identity application 126. For example, the lab technician 204 may either use the individual interface device 206 or the electronic medical records computing device 160 to execute the inclusive identity application 126.

If a serological test is positive or if the individual is administered a vaccine (meaning the patient is immune to a specific disease), the lab technician 204 uses the individual interface device 206 or the electronic medical records computing device 160 to capture one or more biometrics of the individual (e.g., use biometric capture circuitry to capture face, palm, and/or fingerprint biometrics) and generates a unique biometric token based on the one or more biometrics of the individual.

The lab technician 204 submits this biometric token, the test result, the name of the diagnostic lab 202 that performed the test, and the date of the test to the central server 212. All other personally identifiable information associated with the individual will be stored at the diagnostic lab 202, as per normal procedure—in the paper file 208 or in the electronic medical records computing device 210, and according to local laws and regulations.

The central server 212 stores the biometric token, the test result, the name of the diagnostic lab 202, and date of the test in a database (e.g., the global ledger 108). The centralized server also makes the biometric token accessible for queries to various checkers via one or more application programming interfaces (APIs).

When a checker needs to audit the veracity of the test result, the checker may use the biometric token to request the diagnostic lab 202 to share the underlying medical records associated with the individual that generated the biometric token. With access to the underlying medical records, the checker may then identify the individual in question and require re-testing of the individual for immunity.

A checker that needs to authenticate the COVID-19 immunity of an applicant would also have access to the inclusive identity application 126. At the point of a validation request, the checker may use one of the plurality of individual interface devices 214A-214C to capture one or more biometrics of the individual, generate the biometric token, and submit the biometric token via the API to the central server 212. If the individual is immune, there will be a match at the central server 212 and the one of the plurality of individual interface devices 214A-214C will show that match (either in text or symbol). No additional information regarding the individual needs to be shared with the checker.

However, while no additional information regarding the individual needs to be shared with the checker, there is a potential issue with the need to check every biometric token in the central server 212 to find a match. To reduce the computational burden on the central server 212, the checker may include additional information to narrow the search in the database of the central server 212. For example, at the time of submitting the test results to the central server 212, the diagnostic lab 202 may include the state and country code of the diagnostic lab 202 in addition to the name of the diagnostic lab 202 doing the test. At the time the checker takes the individual's biometric, the checker may request the individual to state where the test was performed.

Additionally, in some examples, at the time of the test, the diagnostic lab 202 may ask the individual if the individual anticipates to use the test for international travel. When international travel is anticipated, the diagnostic lab 202 may add an optional flag to the individual's centralized file stored t the central server 212. In these examples, if the checker was representing an international request (e.g., an immigration official at a border), a request back to the central server 212 prioritizes searching against individuals that have been optionally flagged as anticipating international travel. This additional information could also be used as a double-check for the information being searched.

The additional information is not limited to the above examples of additional information. The additional information may include any information that narrows down the search for the individual in the central server 212. However, the additional information may intentionally avoid the issuance of a physical token (card) or virtual token (mobile device based) because there may be potential downsides in production, distribution, servicing challenges. Moreover, the additional information that is embodied in a physical token or a virtual token may also introduce potentially more information at the point of interest, which increases the risk of a nefarious actor being able to map the content of the health status back to the individual (name on card, ownership of the phone).

The central server 212 is not limited to storing information a single disease and is not limited to being accessed by a single checker, which increases the risk that nefarious actors may query the central server 212 without justification. In some examples, to address unjustified queries, the central server 212 may implement a "permissioned database" on the checker-side to ensure only those checkers with a need to know may query the central server 212. For example, an immigration officer might be able to access the central server 212 to confirm whether the individual has immunity to COVID-19 and Yellow Fever, but a senior center home may only access the central server 212 to confirm whether the individual has COVID-19 immunity.

In other examples, to address unjustified queries, the central server 212 may create a permanent record of queries that is accessible by the individual, so that the individual knows who, when, and for what reason the central server 212 was queried with respect the individual. This could deter nefarious actors from surreptitiously taking the individual's biometrics and querying the central server 212 without the individual's permission.

Immigration check points typically have fingerprint scanners. The biometric tokens generated by the inclusive identity application 126 provide interoperability between collection of fingerprints (and other biometric information) at the diagnostic lab 102 and the fingerprints captured at the immigration checkpoint using existing hardware. In other words, no new biometric hardware is required for immigration checkpoints only the addition of a computing device that is capable of executing the inclusive identity application 126.

The system 200 described herein also does not require significant changes in operations or regulations at the lab or governmental level. For example, the system 200 as described herein does not require robust connectivity at the diagnostic lab 202 because the biometric tokens and results may be periodically uploaded in batches to the central server 212. However, the system 200 does require real-time or near real-time connectivity for checkers to query the central server 212 for authentication, unless the physical or virtual tokens are implemented.

Figure 3:
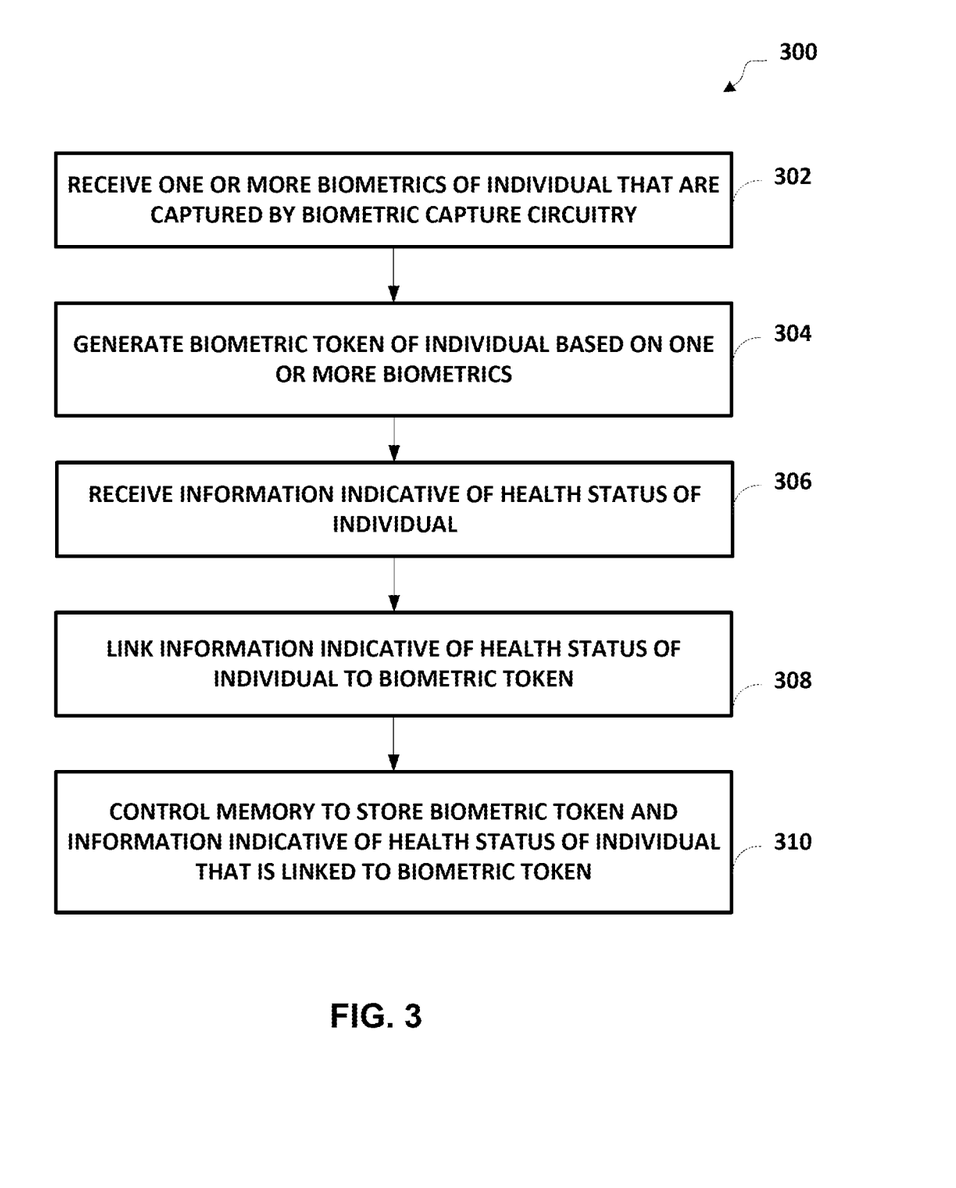
FIG. 3 is a flowchart illustrating an example method performed by the individual interface device of FIG. 1, in accordance with various aspects of the present disclosure.

FIG. 3 is a flowchart illustrating an example method 300 performed by the individual interface device 120 of FIG. 1. In the example of FIG. 3, the method 300 includes the electronic processor 122 receiving one or more biometrics of an individual that are captured by the biometric capture circuitry 136 (at block 302).

In the example of FIG. 3, the method 300 includes the electronic processor 122 generating a biometric token of the individual based on the one or more biometrics (at block 304).

In the example of FIG. 3, the method 300 includes the electronic processor 122 receiving information indicative of a health status of the individual (at block 306).

In the example of FIG. 3, the method 300 includes the electronic processor 122 linking the information indicative of the health status of the individual to the biometric token (at block 308). The information indicative of the health status of the individual that is linked to the biometric token is biometrically-linked electronic proof of the health status of the individual.

In the example of FIG. 3, the method 300 includes the electronic processor 122 controlling a memory to store the biometric token and the information indicative of the health status of the individual that is linked to the biometric token (at block 310). In some examples, controlling the memory 124 to store the biometric token and the information indicative of the health status of the individual that is linked to the biometric token. In other examples, controlling a memory of central server to store the biometric token and the information indicative of the health status of the individual that is linked to the biometric token.

In some examples, the method 300 may further include the electronic processor 122 controlling a communication interface to transmit the biometric token to a centralized server via a network and the electronic processor 122 controlling the communication interface to transmit the information indicative of the health status of the individual that is linked to the biometric token to the centralized server via the network. Additionally, in some examples, the method 300 may further include the electronic processor 122 controlling the communication interface to receive the health status of the individual from an electronic medical record computing device.

In some examples, the method 300 may further include the electronic processor 122 generating a QR code indicative of the biometric token and the electronic processor 122 controlling a display screen to display the QR code.

In some examples, the health status of the individual may be one selected from a group consisting of: test results of a serological test, and an immunization record of a specific vaccination. Lastly, in some examples, the biometric token and the information indicative of the health status of the individual are not reflective of any sensitive personally identifiable information with respect to the individual.

Figure 4:
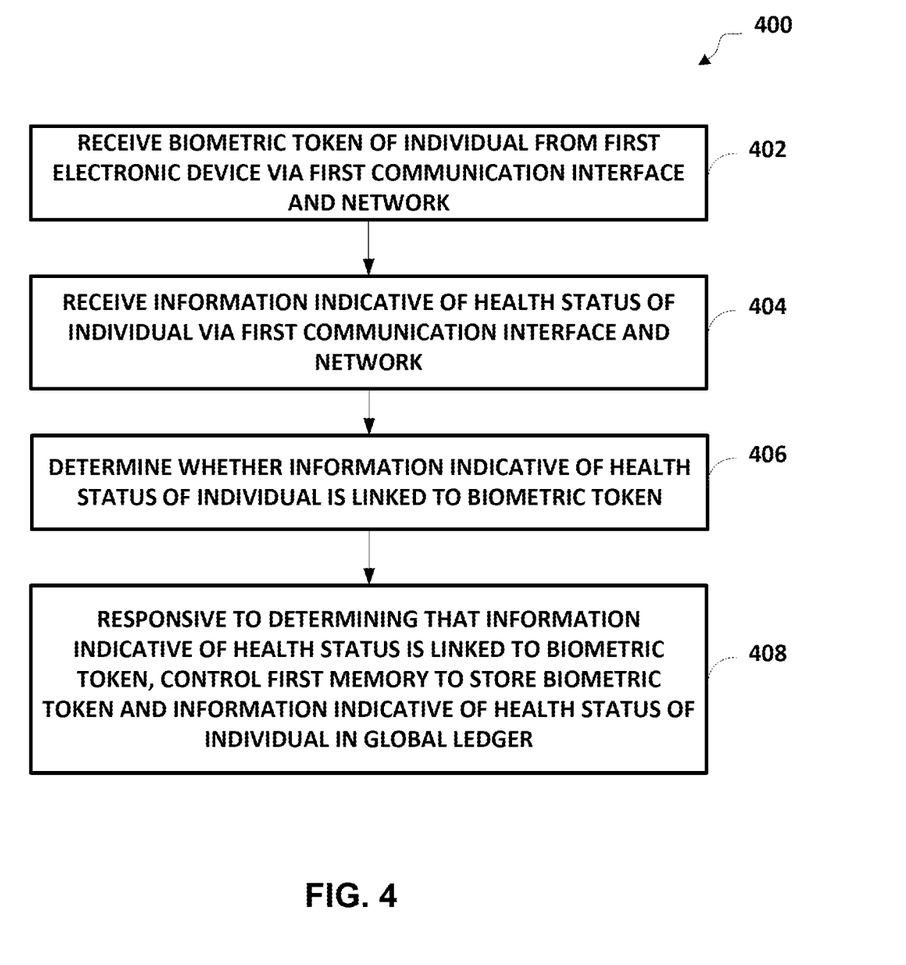
FIG. 4 is a flowchart illustrating an example method performed by the server of FIG. 1, in accordance with various aspects of the present disclosure.

FIG. 4 is a flowchart illustrating an example method 400 performed by the server 100 of FIG. 1. In the example of FIG. 4, the method 400 includes the electronic processor 102 receiving a biometric token of an individual from the first electronic device (e.g., the individual interface device 120) via the first communication interface 112 and the network 180 (at block 402).

In the example of FIG. 4, the method 400 includes the electronic processor 102 receiving information indicative of a health status of the individual via the first communication interface and the network (at block 404). In some examples, the electronic processor 102 may receive the information indicative of the health status of the individual from the individual interface device 120 via the first communication interface 112 and the network 180. In other examples, the electronic processor 102 may receive the information indicative of the health status of the individual from the electronic medical records computing device 160 via the first communication interface 112 and the network 180.

In the example of FIG. 4, the method 400 includes the electronic processor 102 determining whether the information indicative of the health status of the individual is linked to the biometric token (at block 406).

In the example of FIG. 4, the method 400 includes the electronic processor 102 responsive to determining that the information indicative of the health status is linked to the biometric token, controlling the first memory 104 to store the biometric token and the information indicative of the health status of the individual in the global ledger (at block 408).

In some examples, the method 400 may further include the electronic processor 102 linking the information indicative of the health status of the individual to the biometric token in response to determining that the information indicative of the health status of the individual is not linked to the biometric token, and the electronic processor 102 controlling the first memory to store the biometric token and the information indicative of the health status of the individual that is linked to the biometric token in the global ledger 108.

Additionally, in some examples, the method 400 may further include the electronic processor 102 determining whether the biometric token matches one or more biometric tokens in the global ledger 108, and linking the biometric token to the one or more biometric tokens in response to determining that the biometric token matches the one or more biometric tokens in the global ledger 108.

Figure 5:
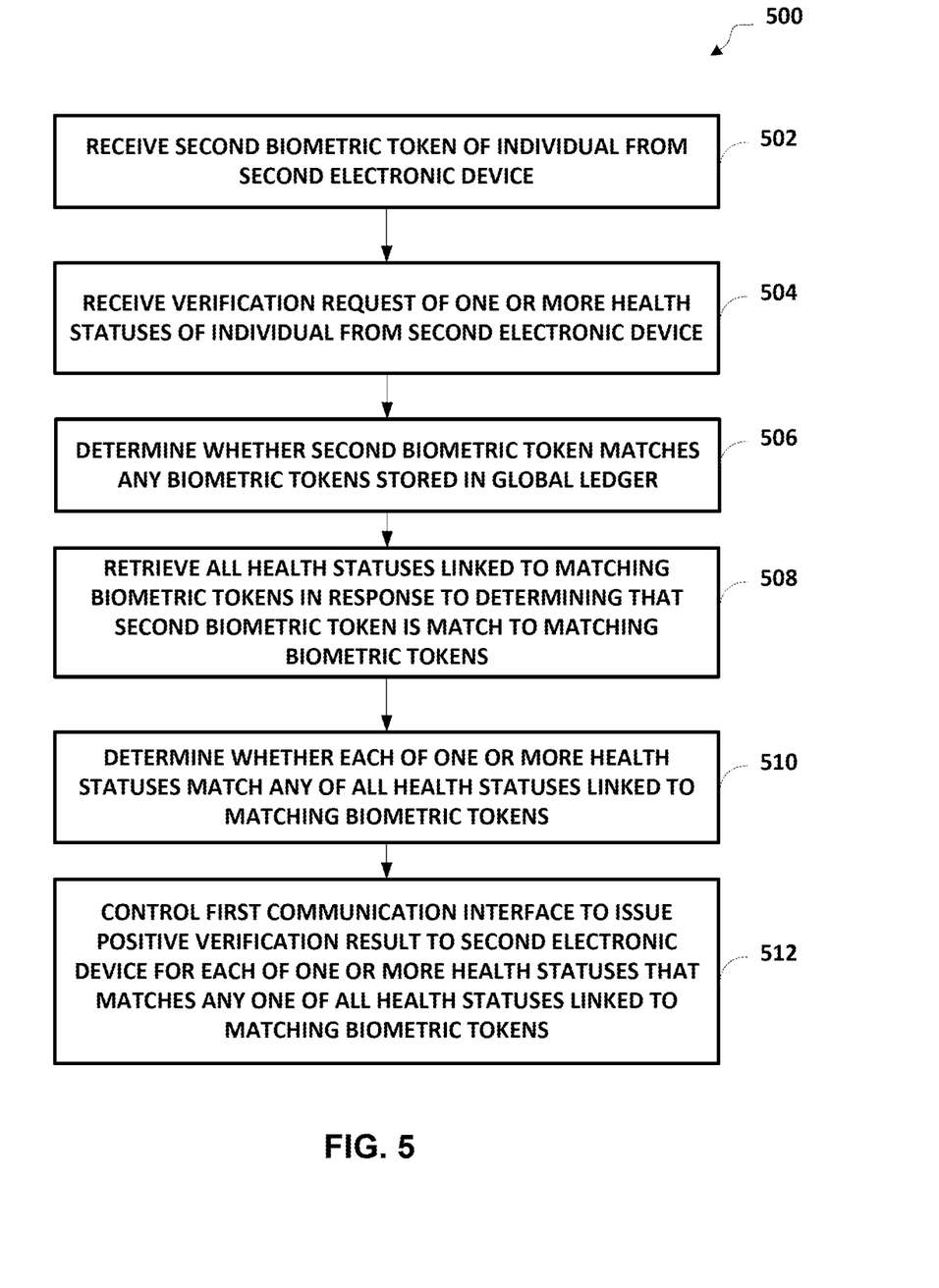
FIG. 5 is a flowchart illustrating an example method performed by the server of FIG. 1, in accordance with various aspects of the present disclosure.

FIG. 5 is a flowchart illustrating an example method 500 performed by the server 100 of FIG. 1. The example method 500 is an extension of the example method 400 described in FIG. 4.

In the example of FIG. 5, the method 500 includes the electronic processor 102 receiving a second biometric token of the individual from the second electronic device (e.g., the individual interface device 120) (at block 502).

In the example of FIG. 5, the method 500 includes the electronic processor 102 receiving a verification request of one or more health statuses of the individual from the second electronic device (at block 504).

In the example of FIG. 5, the method 500 includes the electronic processor 102 determining whether the second biometric token matches any biometric tokens stored in the global ledger 108 (at block 506).

In the example of FIG. 5, the method 500 includes the electronic processor 102 retrieving all health statuses linked to matching biometric tokens in response to determining that the second biometric token is a match to the matching biometric tokens (at block 508).

In the example of FIG. 5, the method 500 includes the electronic processor 102 determining whether each of the one or more health statuses match any of the all health statuses linked to the matching biometric tokens (at block 510).

In the example of FIG. 5, the method 500 includes the electronic processor 102 controlling the first communication interface to issue a positive verification result to the second electronic device for the each of the one or more health statuses that match one of the all health statuses linked to the matching biometric tokens (at block 512).

In some examples, the method 500 may further include the electronic processor 102 controlling the first communication interface to issue a negative verification result to the second electronic device for the each of the one or more health statuses that do not match one of the all health statuses linked to the matching biometric tokens.

Thus, the present disclosure provides, among other things, biometrically-linked electronic proof of a health status of an individual. Various features and advantages of the invention are set forth in the following claim.

What is claimed is:

1. An electronic device comprising:
a biometric capture circuitry configured to capture one or more biometrics of an individual;
a memory storing an inclusive identity application;
an electronic processor communicatively connected to the memory and the biometric capture circuitry, the electronic processor, when executing the inclusive identity application, is configured to
receive the one or more biometrics of the individual that are captured by the biometric capture circuitry,
generate a biometric token of the individual based on the one or more biometrics,
receive information indicative of a health status of the individual,
link the information indicative of the health status of the individual to the biometric token, and
control the memory to store the biometric token and the information indicative of the health status of the individual that is linked to the biometric token,
wherein the information indicative of the health status of the individual that is linked to the biometric token is biometrically-linked electronic proof of the health status of the individual; and
a communication interface configured to
transmit the biometric token to a centralized server via a network, and
transmit the information indicative of the health status of the individual that is linked to the biometric token to the centralized server via the network,
wherein the biometric token and the information indicative of the health status of the individual that is linked to the biometric token are stored on the centralized server without storing any sensitive personally identifiable information associated with the individual.

2. The electronic device of claim 1, wherein the communication interface is further configured to receive the health status of the individual from an electronic medical record computing device.

3. The electronic device of claim 1, further comprising:
a display screen,
wherein the electronic processor is further configured to
generate a QR code indicative of the biometric token, and
control the display screen to display the QR code.

4. The electronic device of claim 1, wherein the health status of the individual is one selected from a group consisting of:
test results of a serological test, and
an immunization record of a specific vaccination.

5. A non-transitory computer-readable medium storing instructions that, when executed by an electronic processor, cause the electronic processor to perform a set of operations, the set of operations comprising:
receiving one or more biometrics of an individual that are captured by a biometric capture circuitry;
generating a biometric token of the individual based on the one or more biometrics,
receiving information indicative of a health status of the individual;
linking the information indicative of the health status of the individual to the biometric token;
controlling a memory to store the biometric token and the information indicative of the health status of the individual that is linked to the biometric token;
controlling a communication interface to transmit the biometric token to a centralized server via a network; and
controlling the communication interface to transmit the information indicative of the health status of the individual that is linked to the biometric token to the centralized server via the network,
wherein the information indicative of the health status of the individual that is linked to the biometric token is biometrically-linked electronic proof of the health status of the individual, and
wherein the biometric token and the information indicative of the health status of the individual that is linked to the biometric token are stored on the centralized server without storing any sensitive personally identifiable information associated with the individual.

6. The non-transitory computer-readable medium of claim 5, wherein the set of operations further includes controlling the communication interface to receive the health status of the individual from an electronic medical record computing device.

7. The non-transitory computer-readable medium of claim 5, wherein the set of operations further includes
generating a QR code indicative of the biometric token; and
controlling a display screen to display the QR code.

8. The non-transitory computer-readable medium of claim 5, wherein the health status of the individual is one selected from a group consisting of:
test results of a serological test, and
an immunization record of a specific vaccination.

9. A system comprising:
a network;
a server including
a first communication interface configured to communicate with the network,
a first electronic processor, and
a first memory including an immunization collection and issuance program and a global ledger; and
a first electronic device communicatively connected to the network,
wherein the first electronic processor, when executing the immunization collection and issuance program, is configured to
receive a biometric token based on one or more biometrics of an individual from the first electronic device via the first communication interface and the network,
receive information indicative of a health status of the individual via the first communication interface and the network,
determine whether the information indicative of the health status of the individual is linked to the biometric token, and
responsive to determining that the information indicative of the health status is linked to the biometric token, control the first memory to store the biometric token and the information indicative of the health status of the individual in the global ledger,
wherein the information indicative of the health status of the individual that is linked to the biometric token is biometrically-linked electronic proof of the health status of the individual,
wherein the biometric token and the information indicative of the health status of the individual that is linked to the biometric token are stored on the centralized server without storing any sensitive personally identifiable information associated with the individual.

10. The system of claim 9, wherein the first electronic processor is further configured to
   link the information indicative of the health status of the individual to the biometric token in response to determining that the information indicative of the health status of the individual is not linked to the biometric token, and
   control the first memory to store the biometric token and the information indicative of the health status of the individual that is linked to the biometric token in the global ledger.

11. The system of claim 9, wherein the first electronic processor is further configured to determine whether the biometric token matches one or more biometric tokens in the global ledger, and
   link the biometric token to the one or more biometric tokens in response to determining that the biometric token matches the one or more biometric tokens in the global ledger.

12. The system of claim 9, further comprising:
   a second electronic device communicatively connected to the network,
   wherein the first communication interface is configured to
      receive a second biometric token of the individual from the second electronic device, and
      receive a verification request of one or more health statuses of the individual from the second electronic device, and
   wherein the first electronic processor is configured to
      determine whether the second biometric token matches any biometric tokens stored in the global ledger,
      retrieve all health statuses linked to matching biometric tokens in response to determining that the second biometric token is a match to the matching biometric tokens,
      determine whether each of the one or more health statuses match any of the all health statuses linked to the matching biometric tokens, and
      control the first communication interface to issue a positive verification result for the each of the one or more health statuses that matches one of the all health statuses linked to the matching biometric tokens.

13. The system of claim 12, wherein the one or more health statuses of the individual is one or more selected from a group consisting of:
   test results of a serological test, and
   an immunization record of a specific vaccination.

14. The system of claim 12, wherein the second electronic device is the same device as the first electronic device.

15. The system of claim 9, wherein the first electronic device further includes
   a biometric capture circuitry configured to capture the one or more biometrics of the individual;
   a second memory storing an inclusive identity application; and
   a second electronic processor communicatively connected to the second memory and the biometric capture circuitry, the second electronic processor, when executing the inclusive identity application, is configured to
      receive the one or more biometrics of the individual that are captured by the biometric capture circuitry,
      generate the biometric token of the individual based on the one or more biometrics,
      receive the information indicative of the health status of the individual,
      link the information indicative of the health status of the individual to the biometric token, and
      control the second memory to store the biometric token and the information indicative of the health status of the individual that is linked to the biometric token.

16. The system of claim 9, wherein the server is a remote server that is remote from a user of the first electronic device.

17. The electronic device of claim 1, wherein the centralized server includes a global ledger.

\* \* \* \* \*